US008015862B2

(12) United States Patent
Bollinger et al.

(10) Patent No.: US 8,015,862 B2
(45) Date of Patent: Sep. 13, 2011

(54) METHOD AND DEVICE FOR OPERATING A PARTICLE SENSOR

(75) Inventors: Steve Bollinger, Granger, IN (US); Manfred Weigl, Viehhausen (DE)

(73) Assignee: Continental Automotive GmbH, Hannover (DE)

( * ) Notice: Subject to any disclaimer, the term of this patent is extended or adjusted under 35 U.S.C. 154(b) by 145 days.

(21) Appl. No.: 12/496,511

(22) Filed: Jul. 1, 2009

(65) Prior Publication Data

US 2010/0031733 A1    Feb. 11, 2010

(30) Foreign Application Priority Data

Jul. 4, 2008   (DE) .......................... 10 2008 031 648

(51) Int. Cl.
*G01M 15/10* (2006.01)
(52) U.S. Cl. .................... 73/114.69; 73/28.04
(58) Field of Classification Search .............. 73/23.33, 73/28.04, 114.69, 114.71
See application file for complete search history.

(56) References Cited

U.S. PATENT DOCUMENTS

| 3,886,785 | A | * | 6/1975 | Stadler et al. ............... 73/31.05 |
| 4,307,061 | A | * | 12/1981 | Sarholz ............................ 422/94 |
| 6,466,022 | B1 | | 10/2002 | Koopmans |
| 6,634,210 | B1 | * | 10/2003 | Bosch et al. ................. 73/23.33 |
| 6,949,874 | B2 | | 9/2005 | Schumann |
| 7,350,398 | B2 | * | 4/2008 | Gardiner ...................... 73/28.01 |
| 7,574,895 | B2 | * | 8/2009 | Schnell et al. ............... 73/28.01 |
| 7,609,068 | B2 | * | 10/2009 | Ripley ........................... 324/512 |
| 7,707,875 | B2 | * | 5/2010 | Lee .............................. 73/114.71 |
| 7,770,432 | B2 | * | 8/2010 | Roesch et al. ................ 73/23.33 |
| 7,872,466 | B2 | * | 1/2011 | Dorfmueller et al. ....... 324/71.4 |
| 2001/0035044 | A1 | | 11/2001 | Larsson et al. |
| 2008/0024111 | A1 | | 1/2008 | Dorfmueller et al. |
| 2008/0041138 | A1 | | 2/2008 | Marra |
| 2009/0090622 | A1 | * | 4/2009 | Ripley ........................... 204/401 |

FOREIGN PATENT DOCUMENTS

| DE | 101 24 907 A1 | 11/2002 |
| DE | 102 19 798 A1 | 11/2003 |
| DE | 10 2005 039 915 A | 3/2007 |
| DE | 10 2006 048 354 A1 | 4/2008 |
| EP | 1 036 268 B1 | 1/2004 |
| WO | WO 2006 061 278 A1 | 6/2006 |

OTHER PUBLICATIONS

Braess & Seifert; book: "Vieweg Handbuch für Kraftfahrzeug"; Sep. 2005; 4th edition; Vieweg-Verlag; cover, bibliography, p. 305; Wiesbaden, Germany.

* cited by examiner

*Primary Examiner* — Freddie Kirkland, III
(74) *Attorney, Agent, or Firm* — Cozen O'Connor

(57) ABSTRACT

Method and device for operating a particle sensor arranged in an exhaust tract of an internal combustion engine of a motor vehicle. The particle sensor including a sensor carrier having two sensor electrodes arranged at a predetermined distance from one another on one side of the sensor carrier. The two sensor electrodes are exposed to an exhaust gas stream in the exhaust tract. The at least two sensor electrodes are acted upon with a collective potential, the collective potential having a value such that electrically charged particles are attracted out of the exhaust gas stream in the exhaust tract. The attracted particles in this case accumulate on and/or between the two sensor electrodes.

18 Claims, 3 Drawing Sheets

METHOD AND DEVICE FOR OPERATING A PARTICLE SENSOR

BACKGROUND OF THE INVENTION

1. Field of the Invention

The invention relates to a method and a device for operating a particle sensor arranged in an exhaust tract of an internal combustion engine of a motor vehicle comprising a sensor carrier. At least two sensor electrodes are arranged at a predetermined distance from one another on the sensor carrier on one side of the sensor carrier. The at least two sensor electrodes are exposed to an exhaust gas stream in the exhaust tract.

2. Description of the Related Art

Increasingly more stringent statutory regulations for permissible pollutant emissions of motor vehicles in which internal combustion engines are arranged make it necessary to keep the pollutant emissions as low as possible when the internal combustion engine is in operation. This may be carried out by reducing the pollutant emissions occurring during the combustion of the air/fuel mixture in the respective cylinder of the internal combustion engine. Exhaust gas treatment systems are also used which reduce the pollutant emissions during the combustion processes, for example through the filtration and combustion of soot particles in diesel internal combustion engines (see the manual "Vieweg Handbuch Kraftfahrzeugtechnik" ["Vieweg Motor Vehicle Technology Handbook"] by Braess and Seiffert, Fourth Edition, published by the Vieweg-Verlag, page 305).

SUMMARY OF THE INVENTION

An object of the invention is a method and device for operating a particle sensor that provides reliable and cost-effective detection of particles in an exhaust gas stream.

One embodiment of the invention is a method and a corresponding device for operating a particle sensor arranged in an exhaust tract of an internal combustion engine of a motor vehicle.

The particle sensor comprises a sensor carrier on which at least two sensor electrodes are arranged at a predetermined distance from one another on one side of the sensor carrier. The at least two sensor electrodes are exposed to an exhaust gas stream in the exhaust tract.

The at least two sensor electrodes are acted upon with a substantially identical collective potential. The collective potential has a value such that electrically charged particles, beyond a stipulated particle size, are attracted out of the exhaust gas stream in the exhaust tract and accumulate on and/or between the at least two sensor electrodes. Operating the particle sensor in this way, particularly small particles, from a particle size of 50 nm are detected by the particle sensor. Therefore the particle sensor has a particularly high sensitivity. The particle sensor is preferably arranged downstream of a particle filter to monitor the particle filter.

The at least two sensor electrodes are preferably arranged in a comb structure with respect to one another and are preferably at a distance from one another, between their respective comb fingers, of a few µm, for example, 10 µm.

The collective potential has, as compared with a reference potential, a high potential value of preferably 1 kV, so that electrically charged particles are attracted out of the exhaust gas stream. The collective potential with which the at least two sensor electrodes are acted upon is preferably substantially identical. In one embodiment, a non-identical collective potential with a predetermined potential difference of 5 V between the at least two sensor electrodes is used. A potential difference is required to determine a resistance value between the at least two sensor electrodes. The electrically charged particles may be charged positively or negatively. The electrical charge of the particles is induced by friction with other particles in the exhaust gas stream. Alternatively, the particles are electrically charged upstream of the particle sensor by a corona. Particles from a particularly small particle size are detected particularly reliably.

In one embodiment, during action by the substantially identical collective potential, a resistance value between the at least two electrodes is determined. The substantially identical collective potential, with which the at least two sensor electrodes are acted upon, has a predetermined potential difference between the at least two sensor electrodes so that a value of a resistance between the sensor electrodes is determined if a particle layer has accumulated on and/or between the at least two sensor electrodes. The determined value of the resistance is representative of a layer thickness of particles on and/or between the at least two sensor electrodes. Thus, depending on the determined resistance value, evidence of a particle concentration in the exhaust gas stream can be obtained particularly simply and reliably. Furthermore, for example, reliable evidence of the functioning capacity of the particle filter which is preferably arranged upstream of the particle sensor can be obtained.

In one embodiment, the at least two sensor electrodes are acted upon by the substantially identical collective potential for a preset or stipulated collective duration. After the collective duration, a determining voltage is applied between the at least two sensor electrodes. A determining current is detected as a function of the detected particles and of the determining voltage. A resistance value between the at least two sensor electrodes is determined as a function of the determining voltage and of the determining current. The at least two sensor electrodes are preferably acted upon by a substantially identical collective potential, such as 1 kV, for the collective duration. After the collective duration, the at least two sensor electrodes are not acted upon any further by the substantially identical collective potential. After the collective duration, the determining voltage, such as 5 V, is applied between the at least two sensor electrodes. The value of the determining voltage is assigned to the potential difference with which the collective potential is acted upon. This results in a particularly simple determination of the resistance between the at least two sensor electrodes. Evidence of a particle concentration in the exhaust gas stream can be obtained as a function of the determined resistance and of the collective duration. The action of the essentially identical collective potential upon the at least two sensor electrodes is designated as the collective phase, and subsequent application of the determining voltage and the determination of the resistance value is designated as the determining phase.

In one embodiment of the invention, an operating state of the internal combustion engine is determined. In this case, the collective duration is preset or stipulated as a function of the determined operating state of the internal combustion engine. For example, a dynamic operating state of the internal combustion engine for example, during an accelerating action of the motor vehicle, is determined as an operating state. Particularly during the accelerating action of the motor vehicle, the internal combustion engine has a particularly high emission of particles, such as soot particles. Therefore, during this operating state, the collective duration is preferably shortened for example, for a few seconds, because an accumulation of the particles on the particle sensor takes place particularly quickly due to the high particle concentration. During a stationary operating state of the internal combustion engine for example, when the internal combustion engine is operating at a constant rotational speed, the collective duration is preferably lengthened for example, for a few minutes. In this case, the internal combustion engine has a low emission of particles, as compared with the accelerating action.

In one embodiment, the particle sensor is heated to a preset or stipulated temperature during the collective duration and/or during the determining of the resistance value. During the collective phase and/or during the determining phase, it may be necessary to heat the particle sensor to a stipulated temperature to avoid condensation and therefore a depositing of condensate, such as water, on and/or between the at least two sensor electrodes, thereby distorting or falsifying the determination of the resistance between the at least two sensor electrodes. This allows a particularly reliable operation of the particle sensor and therefore a reliable detection of the particles in the exhaust gas stream.

In one embodiment, the particle sensor is heated such that particles continue to accumulate on the particle sensor. This ensures that particles are reliably detected and that the accumulated particles are not burnt.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Exemplary embodiments of the invention are explained in more detail below with reference to the diagrammatic drawings in which.

DETAILED DESCRIPTION OF THE PRESENTLY PREFERRED EMBODIMENTS

Elements of identical design or function are identified throughout the figures by the same reference symbols.

Figure 1:
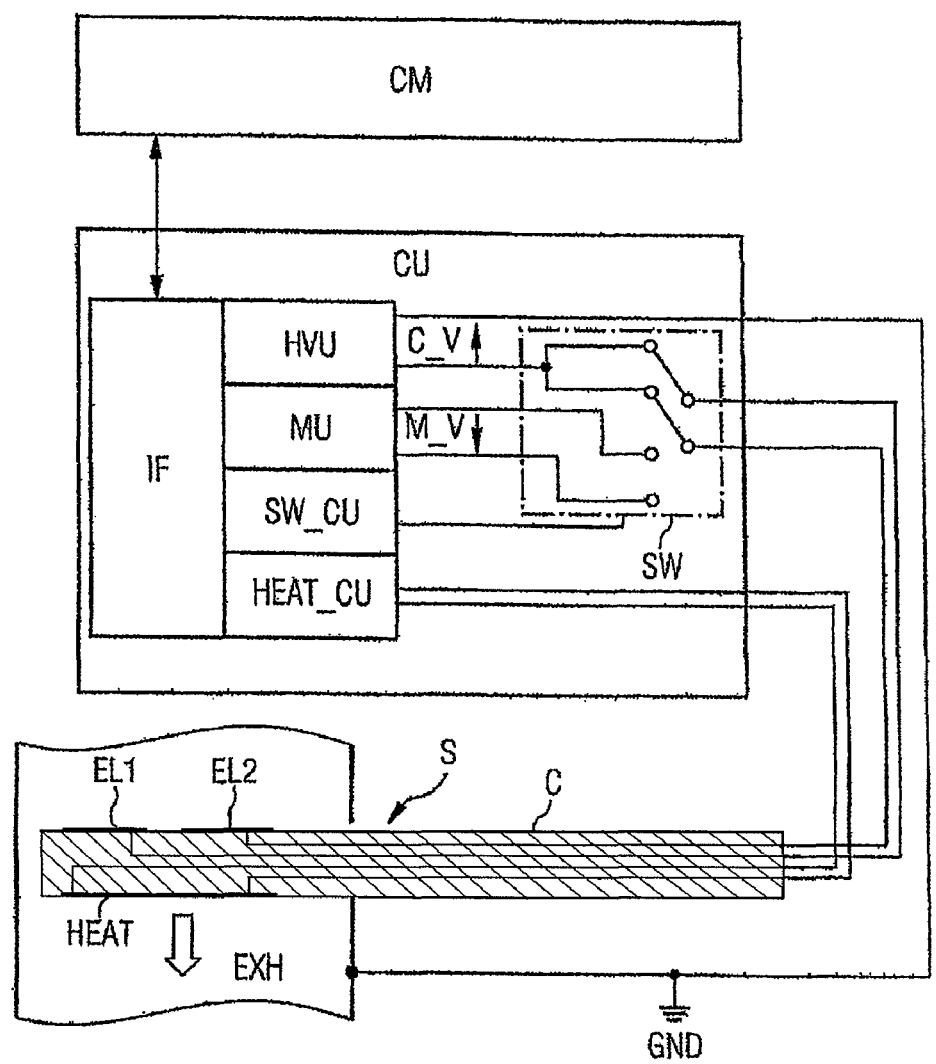
FIG. 1 is a particle sensor according to the invention.

In FIG. 1, a particle sensor S is arranged at least partially in an exhaust tract EXH of an internal combustion engine of a motor vehicle. Preferably, the particle sensor S is arranged downstream of a particle filter of the motor vehicle. The particle sensor S comprises a sensor carrier C, which is preferably designed as a glass or ceramic carrier. A first and a second sensor electrode EL1 and EL2 are arranged on one side of the sensor carrier C on one side such that they are exposed to the exhaust gas stream in the exhaust tract EXH. The direction of the exhaust gas stream is identified in FIG. 1 by an arrow in the exhaust tract EXH for clearer understanding. The particle sensor S is preferably oriented in the exhaust tract EXH such that the first and the second sensor electrodes EL1 and EL2 face upstream. The sensor electrodes EL1 and EL2 are preferably designed as platinum electrodes. Other orientations of the particle sensor S in the exhaust tract EXH and other versions of the sensor electrodes EL1 and EL2 are also envisaged.

A heating element HEAT is arranged on a side of the particle sensor S that faces away from the sensor electrodes EL1 and EL2. Another arrangement of the heating element HEAT is also basically possible. The first and the second sensor electrodes EL1 and EL2 and the heating element HEAT of the particle sensor S are coupled electrically to a control unit CU.

The control unit CU comprises a switching element SW, a high-voltage unit HVU, a determining unit MU, a switching element control unit SW_CU and a heating element control unit HEAT_CU. Furthermore, the control unit CU has an interface IF which is preferably designed as a communication interface, such as, for example, a CAN interface coupled to a data network of the motor vehicle. The control unit CU is coupled by the interface IF, the control unit CU is coupled, to a control apparatus CM of the motor vehicle. The control unit CU is preferably designed as a microcontroller and preferably comprises a memory that stores at least one program processed by a computing unit of the control unit CU. In one embodiment, the control unit CU designated as a device for operating a particle sensor.

The control apparatus CM of the motor vehicle is preferably designed as an engine control apparatus and is therefore designed to provide or stipulate and/or determine an operating state of the internal combustion engine of the motor vehicle.

The high-voltage unit HVU is designed to apply a collective voltage C_V between the first and the second sensor electrodes EL1 and EL2 and a metal border of the exhaust tract EXH during a collective phase as a function of a switching position of the switching element SW. The first and the second sensor electrodes EL1 and EL2 are acted upon with an essentially identical potential which may also be designated as a collective potential. The collective voltage C_V is preferably a high voltage having a value of 1 kV. The metal border of the exhaust tract EXH is preferably coupled to a reference potential GND which is the ground of the motor vehicle. Alternatively, it is possible to assign the reference potential GND to the first and the second sensor electrodes EL1 and EL2 and the collective potential to the metal border of the exhaust tract EXH. During action upon the first and the second sensor electrode EL1 and EL2 with the collective potential electrically charged particles, such as, for example, soot particles, preferably greater than or equal to 50 nm, are attracted and accumulated on and/or between the first and the second sensor electrodes EL1 and EL2. The electrically charged particles are charged positively or negatively. The collective potential and the electrically charged particles to be detected ideally having opposite polarities. The particles are charged electrically due to friction with other particles in the exhaust gas stream. Alternatively, however, it is also possible to charge the particles electrically before their detection by the particle sensor S by a corona that is preferably arranged downstream of the particle filter and upstream of the particle sensor S in the exhaust tract EXH of the internal combustion engine. When the electrically charged particles impinge onto the sensor carrier C between the first and the second sensor electrodes EL1 and EL2, charge equalization occurs.

The determining unit MU is configured to apply a determining voltage M_V, for example 5V, between the first and the second sensor electrodes EL1 and EL2 during a determining phase as a function of the switching position of the switching element SW. The determining unit MU is configured to detect a determining current as a function of the determining voltage M_V and of the accumulated particles on and/or between the first and second sensor electrodes EL1 and EL2 and to determine an electrical resistance RS between the first and the second sensor electrodes EL1 and EL2 as a function of the determining voltage and of the determining current.

Preferably, the electrical resistance RS between the first and the second sensor electrodes EL1 and EL2 has a significantly higher resistance value in the case of a regenerated or purified particle sensor S than in the case of a non-purified particle sensor. When particles accumulate between the first and the second sensor electrodes EL1 and EL2, the value of the electrical resistance RS falls. The electrical resistance RS is therefore dependent on a thickness of a particle layer which has accumulated on and/or between the first and the second sensor electrodes EL1 and EL2. If the thickness of the particle layer overshoots a limit thickness, a further growth in the thickness of the particle layer typically does not lead to any further appreciable variation in the electrical resistance RS between the first and the second sensor electrodes EL1 and EL2. The determined resistance RS in the case of a limit thickness of the particle layer is preferably designated as a limit resistance having a value of 5 kOhm.

The switching element control unit SW_CU is designed to activate the switching element SW, preferably as a function of the processing of the at least one program in the data store of the control unit CU.

The heating element control unit HEAT_CU is designed to activate the heating element HEAT on the particle sensor S. Activation preferably occurs such that during the collective and the determining phase, the particle sensor S is heated to a predetermined temperature, preferably 300° C. to 400° C. The advantage of this is that no condensate settles on and/or between the first and the second sensor electrodes EL1 and EL2, thereby skewing or falsifying the determination of the electrical resistance RS between the first and the second sensor electrodes EL1 and EL2. In this case, the temperature is preset such that particles are detected by the particle sensor S and the particles which have already accumulated are not burnt. The heating element control unit HEAT_CU is designed to activate the heating element HEAT of the particle sensor S such that the accumulated particles on the particle sensor S are burnt and therefore the particle sensor S is regenerated. Preferably, such activation of the heating element HEAT takes place when the limit thickness of the particle layer on and/or between the first and the second sensor electrodes EL1 and EL2 is reached or overshot. A heating of the particle sensor S to 800° C. is typically necessary for the combustion of the particles.

Figure 2:
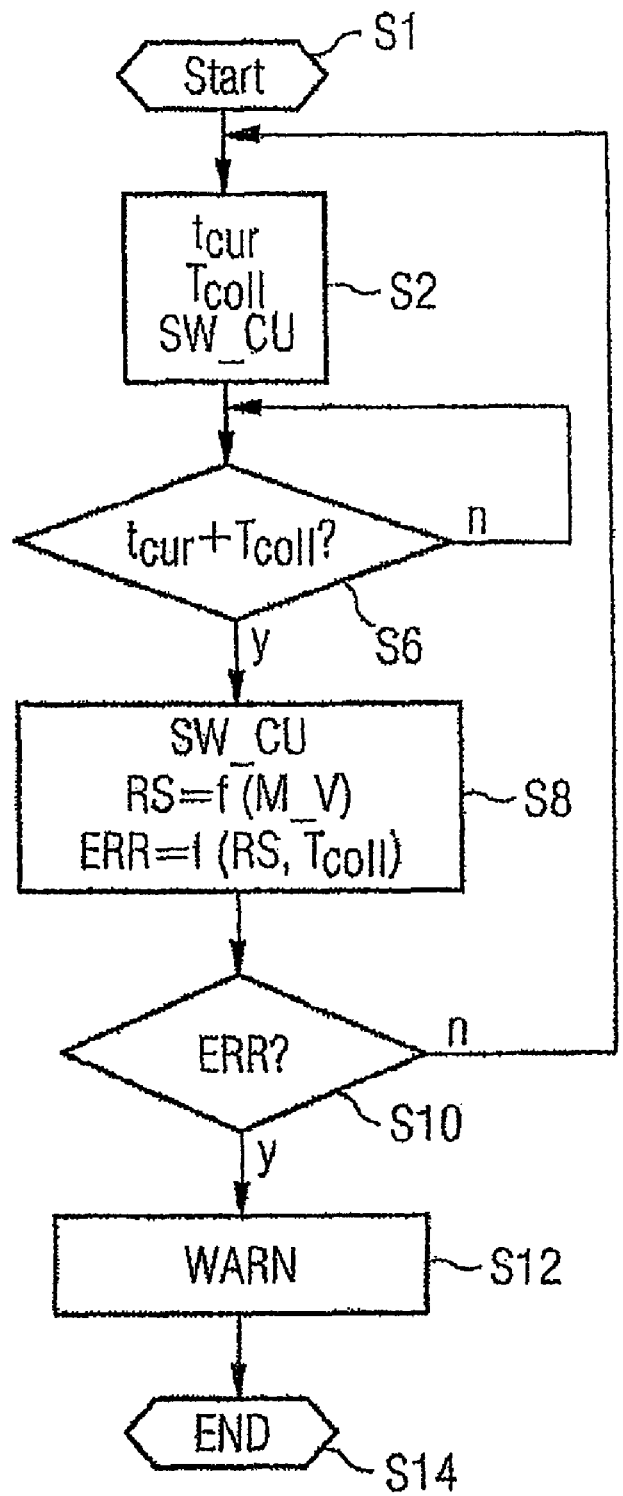
FIG. 2 is a flow chart.

FIG. 2 illustrates a program which is preferably processed by the computing unit of the control unit CU to operate the particle sensor S. The program is started in a first step S1. In a step S2, the collective phase is started and the switching element SW is activated by means of the switching element control unit SW_CU such that the first and the second sensor electrodes EL1 and EL2 are electrically coupled to the high-voltage unit HVU and are acted upon by the essentially identical collective potential. A variable tcur is preferably initialized to a current time value, such as a time value of a real time interrupt counter, and a collective duration Tcoll is determined. The collective duration Tcoll is preferably determined as a function of the operating state of the internal combustion engine. For example, a dynamic operating state of the internal combustion engine, such as during an accelerating action of the motor vehicle, may be determined as the operating state. During the accelerating action of the motor vehicle, the internal combustion engine has a particularly high emission of particles. During this operating state, the collective duration is preferably stipulated to be shortened, such as, for example, for a few seconds, because particles have accumulated sufficiently on the particle sensor S, even within this shortened collective duration, in order to carry out a determination of the electrical resistance RS. During a stationary operating state of the internal combustion engine, such as when the internal combustion engine is operating at a constant rotational speed, the collective duration is preferably lengthened for a few minutes, because the particle emission of the internal combustion engine is relatively low in this operating state, as compared with the accelerating action. The collective duration Tcoll is assigned to the collective phase in which the particles from the exhaust gas stream accumulate on and/or between the first and the second sensor electrodes EL1 and EL2.

In a step S6, the value of the variable tcur, added to the collective duration Tcoll, is compared with the current time value. If the value of the variables tcur, added to the collective duration Tcoll, has a value higher than the current time value, step S6 is executed anew. If the value of the variables tcur added to the collective duration Tcoll has a value lower than or equal to the current time value, that is to say the collective duration Tcoll has elapsed, a step S8 is executed. With the lapse of the collective duration Tcoll, the collective phase is ended, and therefore the action upon the first and the second sensor electrode EL1 and EL2 with the essentially identical collective potential.

In step S8, the determining phase is started and therefore the switching element SW is activated by the switching element control unit SW_CU such that the first and the second sensor electrodes EL1 and EL2 are coupled electrically to the determining unit MU and are acted upon with the determining voltage M_V. The determining unit MU is configured to detect the determining current as a function of the particle layer on and/or between the first and the second sensor electrodes EL1 and EL2 and to determine as a function of this the electrical resistance RS between the first and the second sensor electrodes EL1 and EL2. It can be determined, as a function of the determined value of the electrical resistance RS and of the collective duration Tcoll, whether the particle filter arranged upstream of the particle sensor S has a fault ERR. For example, the fault ERR is preferably determined by a comparison of the determined value of the electrical resistance RS with a respective value of a stored resistance value in the data store of the control unit CU. Furthermore, the collective duration Tcoll may be taken into account in order to determine the fault ERR of the particle filter.

In a step S10, it is checked whether the fault ERR of the particle filter is present or whether the particle filter is functioning free of faults. If no fault ERR is present, the program is preferably started anew in step S2. If, by contrast, the fault ERR is present, in a step S12 the fault ERR is signaled to a driver of the motor vehicle, by a warning lamp in a driver information system of the motor vehicle. The program is thereupon terminated in a step S14. Alternatively, however, the program is executed anew in step S2, to preferably confirm the fault ERR of the particle filter. If appropriate, before a renewed execution of step S2, the heating element HEAT is activated by the heating element control unit HEAT_CU such that the accumulated particles are burnt and therefore the particle sensor S is regenerated. Alternatively, the determined electrical resistance RS is compared with the stipulated limit resistance and the heating element HEAT may be activated as a function of the comparison. A regeneration of the particle sensor S takes place, for example, during the heating of the particle sensor S to 800° C. Furthermore, during the processing of the program, the heating element HEAT is activated by the heating element control unit HEAT_CU such that the formation of condensate on the particle sensor S is avoided.

Figure 3:
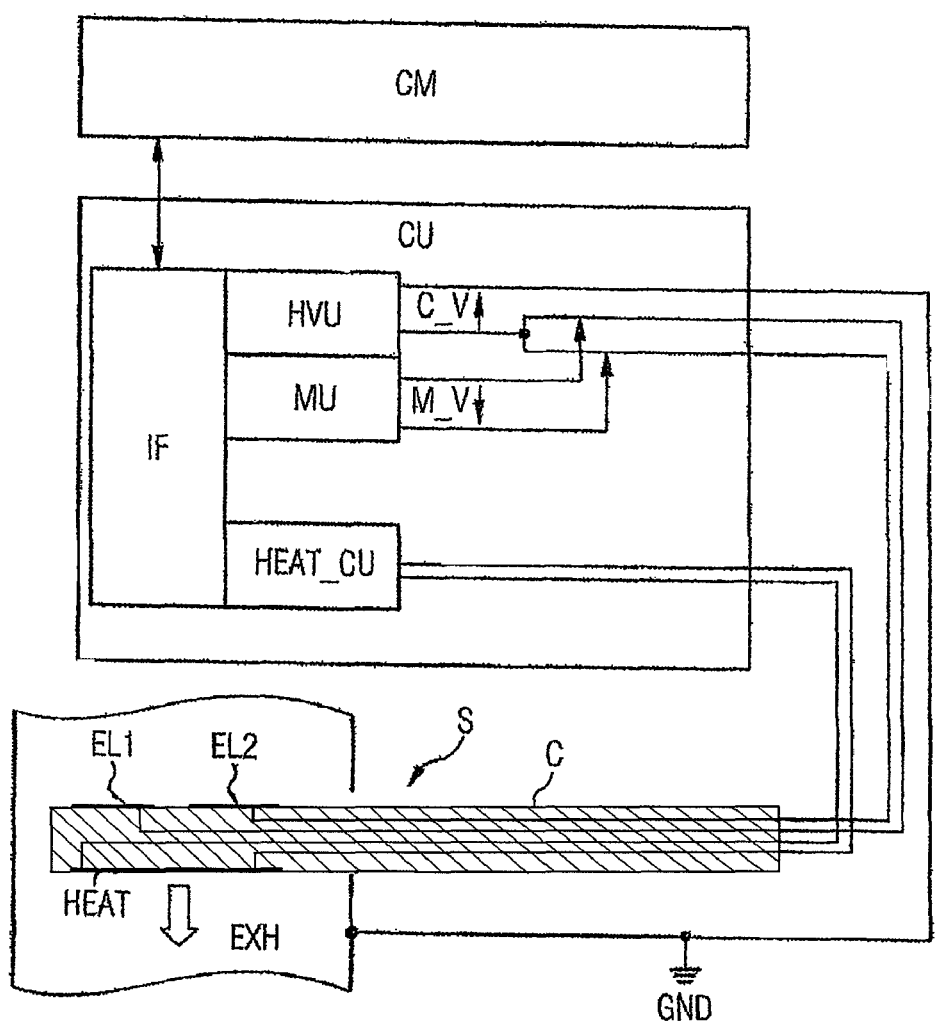
FIG. 3 is a diagrammatic illustration of a particle sensor.

In FIG. 3, the control unit CU is designed such that the determining voltage M_V of the determining unit MU is modulated onto the collective voltage C_V which is made available by the high-voltage unit HVU. That is to say, the first and the second sensor electrodes EL1 and EL2 are acted upon with the essentially identical collective potential, the collective potential having a minimum potential difference, such as, for example, 5 V, between the first and the second sensor electrodes EL1 and EL2. Thus, for example, the first sensor electrode EL1 has a potential of 1000 V, while the second sensor electrode EL2 has a potential of 1005 V. The potential difference between the first and the second sensor electrodes EL1 and EL2 is used to determine the electrical resistance RS between the first and the second sensor electrode EL1 and EL2. This exemplary embodiment allows a continuous determination of the electrical resistance RS between the first and the second sensor electrodes EL1 and EL2. The separate collective phase and determining phase are therefore dispensed with. The switching element SW and the switching element control unit SW_CU are not needed Alternatively, however, it is possible to continue to use the switching element SW and the switching element control unit SW_CU, in which case a modulation of the determining voltage M_V onto the collective voltage C_V is independent of the switching position of the switching element SW.

In addition to the direct determination of the electrical resistance RS between the first and the second sensor electrodes EL1 and EL2 as a function of the determining voltage M_V and of the assigned determining current, an ohmic resistance component of an impedance of an overall capacitance can also be used as a representation of a particle concentration, the overall capacitance resulting from the sensor electrodes EL1 and EL2 and from the particle layer. In this case, the first and the second sensor electrodes EL1 and EL2 are preferably coated with an insulating layer consisting of glass or aluminum oxide. The first and the second sensor electrodes EL1 and EL2 preferably have capacitive properties, without an accumulated particle layer, due to their arrangement on the sensor carrier C. A particle layer which accumulates on and/or between the coated first and second sensor electrodes affords a further capacitance, in which case the particle layer may be considered in each case as a first capacitor electrode and the first or second sensor electrode may be considered in each case as a second capacitor electrode. The insulating layer is arranged as a dielectric between the particle layer and the first or second sensor electrode. The overall capacitance thus arises from a series connection of a first capacitance, which results from the first sensor electrode EL1 and the particle layer, and of a second capacitance, which results from the particle layer and the second sensor electrode EL2. In this case, the impedance of the overall capacitance is assigned an ohmic and a complex resistance component, the ohmic resistance component being dependent on the thickness of the particle layer on and/or between the coated first and second sensor electrodes EL1 and EL2. The particle concentration in the exhaust gas stream of the motor vehicle, and therefore the functioning capacity of the particle filter, can be determined as a function of the determination of a value of the ohmic resistance component.

The control unit CU may be arranged as a separate control unit in the motor vehicle. The control unit CU may, however, preferably also be integrated in the control apparatus CM.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for operating a particle sensor arranged in an exhaust tract of an internal combustion engine, the particle sensor comprising a sensor carrier and at least two sensor electrodes arranged at a predetermined distance from one another on a first side of the sensor carrier, the method for operating the particle sensor comprising:
  exposing the at least two sensor electrodes to an exhaust gas stream in the exhaust tract;
  applying a collective potential to each of the at least two sensor electrodes, the collective potential having a value configured to attract electrically charged particles beyond a stipulated particle size out of the exhaust gas stream in the exhaust tract,
  wherein the electrically charged particles accumulate at least one of on the at least two sensor electrodes and between the at least two sensor electrodes.

2. The method for operating a particle sensor according to claim 1, further comprising determining a resistance value between the at least two electrodes while applying the collective voltage.

3. The method for operating a particle sensor according to claim 1, wherein the collective potential is applied to the at least two sensor electrodes for a stipulated collective duration, the method further comprising:
  applying a determining voltage between the at least two sensor electrodes after the collective duration;
  detecting a determining current based at least in part on the accumulated particles and the determining voltage; and
  determining the resistance value between the at least two sensor electrodes as a function of the determining voltage and the determining current.

4. The method for operating a particle sensor according to claim 3, further comprising:
  determining an operating state of the internal combustion engine; and
  setting the collective duration based at least in part on the operating state of the internal combustion engine.

5. The method for operating a particle sensor according to claim 3, further comprising heating the particle sensor to a stipulated temperature during at least one of the collective duration and during the determining of the resistance value.

6. The method for operating a particle sensor according to claim 5, wherein particles continue to accumulate on the particle sensor when the particle sensor is heated.

7. A device for operating a particle sensor arranged in an exhaust tract of an internal combustion engine, comprising a sensor carrier and at least two sensor electrodes arranged on the a sensor carrier at a predetermined distance from one another on a first side of the sensor carrier, the at least two sensor electrodes configured to be exposed to an exhaust gas stream in the exhaust tract,
  the device for operating the particle sensor comprising a switching element and a voltage unit configured to selectively apply a collective potential to each of the at least two sensor electrodes, the collective potential having a value such that electrically charged particles beyond a predetermined particle size are attracted out of the exhaust gas stream to the at least two sensor electrodes, wherein the charged particles accumulate at least one of on the at least two sensor electrodes and between the at least two sensor electrodes.

8. A particle sensor system for an exhaust tract of an internal combustion engine, the particle sensor system comprising:

a particle sensor comprising
   a sensor carrier;
   at least two sensor electrodes arranged on the a sensor carrier at a predetermined distance from one another on a first side of the sensor carrier, the at least two sensor electrodes configured to be exposed to an exhaust gas stream in the exhaust tract; and
a device for operating the particle sensor configured to apply a collective potential to each of the at least two sensor electrodes, the collective potential attracting electrically charged particles beyond a predetermined particle size out of the exhaust gas stream,
wherein the charged particles accumulate at least one of on the at least two sensor electrodes and between the at least two sensor electrodes.

9. The particle sensor system according to claim 8, wherein the at least two sensor electrodes are platinum.

10. The particle sensor system according to claim 8, wherein the device for operating a particle sensor further comprises:

a high voltage unit configured to apply the collective potential to the at least two electrodes; and
a determining unit configured to apply a determining voltage to the at least two electrodes.

11. The particle sensor system according to claim 8, wherein the particle sensor further comprises a heating element arranged on the sensor carrier.

12. The particle sensor system according to claim 11, wherein the device for operating a particle sensor further comprises a heating control unit configured to control the heating element.

13. The particle sensor system according to claim 10, wherein the device for operating a particle sensor further comprises a switch unit configured to apply one of the collective voltage and the determining voltage to the at least two electrodes.

14. The particle sensor system according to claim 10, wherein the collective voltage is about 1KV and the determining voltage is about 5V.

15. The particle sensor system according to claim 8, wherein the carrier is at least one of glass and ceramic.

16. The method for operating a particle sensor according to claim 5, wherein the particle sensor is heated to burn off accumulated particles.

17. The particle sensor system according to claim 8, wherein the at least two electrodes are configured as a comb structure.

18. The particle sensor system according to claim 17, wherein the at least two electrodes have a spacing of 10 μm.

* * * * *